United States Patent [19]

Fischer

[11] Patent Number: 4,841,764
[45] Date of Patent: Jun. 27, 1989

[54] DEVICE FOR A HARDNESS MEASURING INSTRUMENT

[76] Inventor: Helmut Fischer, Industriestrasse 20, 7032 Sindelfingen-6, Fed. Rep. of Germany

[21] Appl. No.: 172,479

[22] Filed: Mar. 24, 1988

[30] Foreign Application Priority Data

Nov. 7, 1987 [DE] Fed. Rep. of Germany ....... 3737910

[51] Int. Cl.⁴ ........................... G01N 3/40; G01N 3/42
[52] U.S. Cl. ....................................... 73/81; 73/150 R
[58] Field of Search .................. 73/81, 78, 573, 150 R

[56] References Cited

U.S. PATENT DOCUMENTS

| | | | |
|---|---|---|---|
| 4,318,297 | 3/1982 | Zaffran et al. | 73/78 |
| 4,671,104 | 6/1987 | Fischer | 73/81 |
| 4,691,559 | 9/1987 | Fischer | 73/81 |

Primary Examiner—Tom Noland

[57] ABSTRACT

Device for a hardness measuring instrument comprises a bar device having one end portion that supports a test body, a middle portion that is pivotable about a pivot center, and a second end portion. The device has a gently lowerable measuring device which works on the basis of probes for measuring the thickness of thin layers. At the second end portion of the bar device there is a movable first part of an oscillation damping device, the longitudinal extension of which is aligned with the direction of movement of the test body.

18 Claims, 7 Drawing Sheets

DEVICE FOR A HARDNESS MEASURING INSTRUMENT

BACKGROUND OF THE INVENTION

Such a device is known from German published specification No. 3501288 (U.S Pat. No. 4,691,559, English specification No. 8503109, Japanese patent application No. 87647/85).

As emerges from the German published specification, page 31, para. 1, last sentence, it is necessary to fit the test body in a "completely impact-free" manner.

The device described therein has the advantage that for the first time in the field of hardness measurement of the thinnest surface layers, it is possible to measure micro-hardness. The method of measurement is non-destructive. In the meantime, however, it has been found that the test body must be fitted in an even more impact-free condition than one might previously have imagined in order to obtain from the device everything which the device can offer in terms of surface hardness measurement and micro-hardness measurement.

OBJECT AND STATEMENT OF THE INVENTION

The object of the invention is to provide a device with which the test body can be even more gently placed on the surface. At the same time, it should still be possible to maintain the technique described in this state of the art. This means that it should be possible to allow penetration of the test body below the surface of the substance to be measure with that probe measuring technique which was used previously when measuring thin coatings. Variations in coating thickness of even less and 1 um should be easily measurable. An introduction to this technique can be found in U.S. Pat. No. 4,671,104 that issued June 9, 1987. The details given in the two published specifications are also valid here.

A further object of the invention is to provide a device of the type mentioned, by which it is even more readily possible to apply the test body so gently that it is possible reproducibly to measure hardness in quite high up layer zones.

According to the invention, these objectives are achieved by the following features:

A bar device has a pair of end portions and a middle portion.

A test body is supported on one end portion of the bar device.

The middle portion of the bar device is pivotable about a pivot center.

A gently lowerable measuring device that works on the basis of probes for measuring the thickness of thin layers is provided.

A movable first part of an oscillation damping device is provided at one end portion of the bar device. And the movable first part has a longitudinal extension aligned with the direction of movement of the test body.

Using the device according to the invention, it is possible to revolve depths of penetration down to 2 to 3 nanometers, representing about 20 atoms diameter.

In addition, the described embodiment has the following advantageous features: With respect to the pivot center, the moment consisting of the weight of the first part of the damping device x a first length of the bar device as far as the pivot center is at least substantially equal to the weight acting at the end portion on the test body side x twice the length of the bar device as far as the pivot center. This feature ensures that the damping device, in its movable part, can also be used as a counterweight so that the weights present on the other side of the pivot center are partly, or if at all possible, completely compensated.

The oscillation damping device is of a type unaffected by position. This makes it possible to measure in any position. Certainly, damping devices which are fluid damped do not work the same way because when working overhead, for example, one would have to seal the fluid, which would produce friction.

The oscillation damping device is passive. In consequence, the damping force is constant. Actually, the effect could be produced also by using an electromagnetic damping device. However, it would not be possible, or would be possible only at considerable cost, to maintain constant the current flowing through such a coil. However, passive damping devices are uncritical in this direction.

The oscialltion damping device comprises permanent magnets. This provides a basis of a particularly simple passive damping device, the more so since permanent magnets are massproduced products which are, on the one hand, very cheap because they are mass-produced and, on the other hand, can be kept very accurate.

The movable first part of the oscillation damping device is an electrically readily conductive metal plate. Particularly good damping is obtained in the form of an eddy current brake.

The metal plate has an effective area that is very flat. The damping force is the same in all positions of the bar device. Of course, it must be taken into account that the magnetic force (and also other forces) vary with the square of the distance. If the metal plate were other than flat, then the force would vary for different positions of the bar device.

The metal plate is a copper plate. This makes is possible on the one hand to produce cheaply while enjoying virtually the same conductivity as with the substantially more expensive silver.

The copper plate consists of high purity copper with a proportion of more than 95% copper. This provides an optimum between price and effect. Such a copper plate is nevertheless sufficiently rigid that it can be maintained in its flat position without the use of any additional strengthening frames or suchlike. Furthermore, where the damping work is concerned, the plate is influenced in its heavy direction, which it can readily withstand.

The copper plate has a side with an area in the range from 5 to 30 sq. cm, particularly between 10 and 20 sq. cm. These areas keep the device sufficiently small and the mass sufficiently low but yet the area is sufficiently large that the magnet forces are able to act.

The device further comprises a housing and a second part of the oscillation damping device rigidly affixed thereto. The second part of the oscillation damping device comprises a rigid, solid carrier device for permanent magnets having outlet and inlet areas. The first part of the oscillation damping device comprises a metal plate having a face thereon. And the outlet and inlet areas of the second oscillation clamping device are spaced a small distance from and opposite the face of the metal plate. These features guarantee that, due to the solid and rigid construction, the otherwise small gaps are always maintained and the metal plate can be brought close to the permanent magnets.

The carrier device comprises at least one plate having a flat front face with depressions in which the permanent magnets are embedded. The permanent magnets are positionally held securely and each plunges to an identical depth into the plate so that the field is homogenous over the area.

The permanent magnets have outer faces aligned with the front face of the plate. This provides for simple means to ensure identical and precise gap conditions.

The permanent magnets are glued in place by an adhesive material. The property of the permanent magnets does not alter, as would be possible if shocks or heat where involved. Furthermore, fewer of the permanent magnets which, of course, tend to split, are rejected.

The permanent magnets are of the same type as the anisotropic permanent magnetic materials consisting of rare earth metal and cobalt. To the Applicant's knowledge, such permanent magnets at present offer the best properties.

The carrier device further comprises a second plate mutually parallel with the first plate. The two mutually parallel plates consist of iron and are rigidly mounted a small distance from each other to form a narrow gap. And, the metal plate is symmetrically disposed in the narrow gap. By these features, the damping effect is enhanced and lateral forces which might have the effect of tilting the bar device are avoided. The pivot center therefore only has to withstand forces in the direction of movement of the test body.

The iron is soft iron. An even better damping effect is provided by this feature. Most importantly, one ought to believe that a magnetic short circuit occurs. The effect is, however, better than if, for instance, aluminum or some other non-magnetic material were to be used for the plates.

By reason of the invention, an aperiodic damping is obtained with a once-only overshoot of about 8%. The best values are obtained if the copper plate has a conductance of about 100% per IACS. With the invention, depth of penetration down to 2 nanometers can be resolved, that is to say down to 20 atoms diameter. The magnets used are virtually unaffected by temperature and their residual magnetism is extremely high.

DESCRIPTION OF THE DRAWINGS

The invention will now be described with reference to a preferred embodiment shown in the accompanying drawings in which.

DESCRIPTION OF A PREFERRED EMBODIMENT

Figure 1:
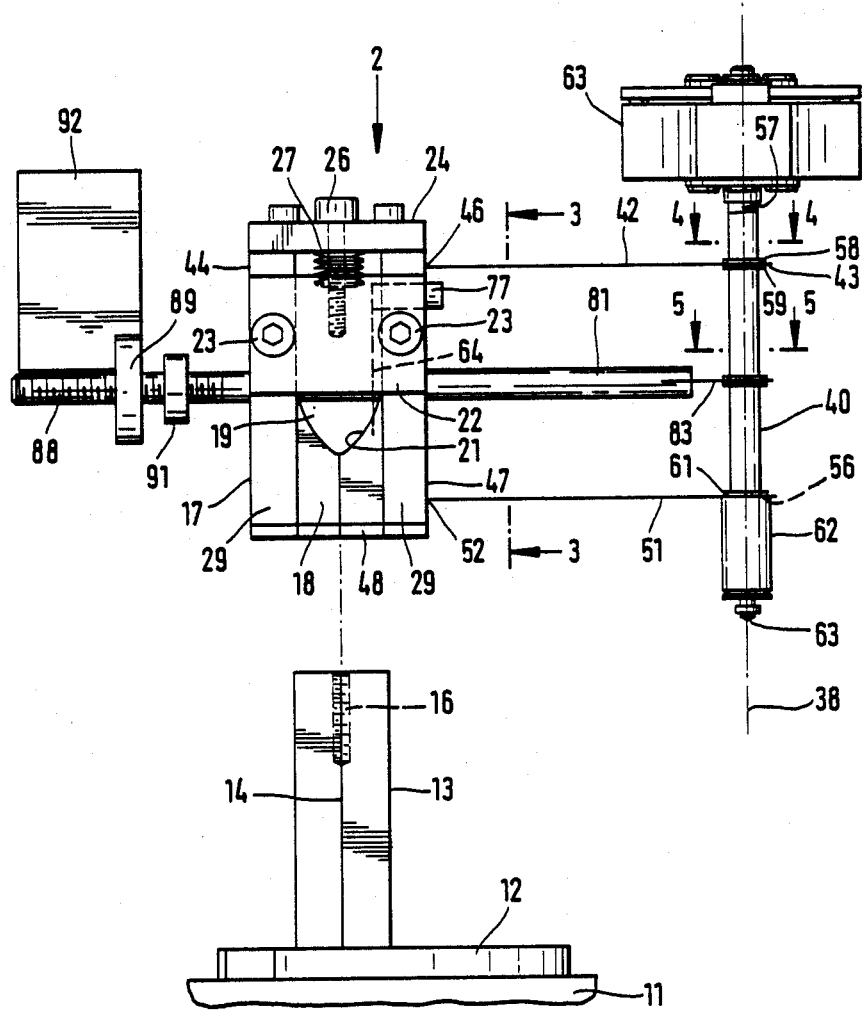
FIG. 1 is a side view of the device according to the invention
in a partly exploded view but showing only a part of the dampng device.
Figure 2:
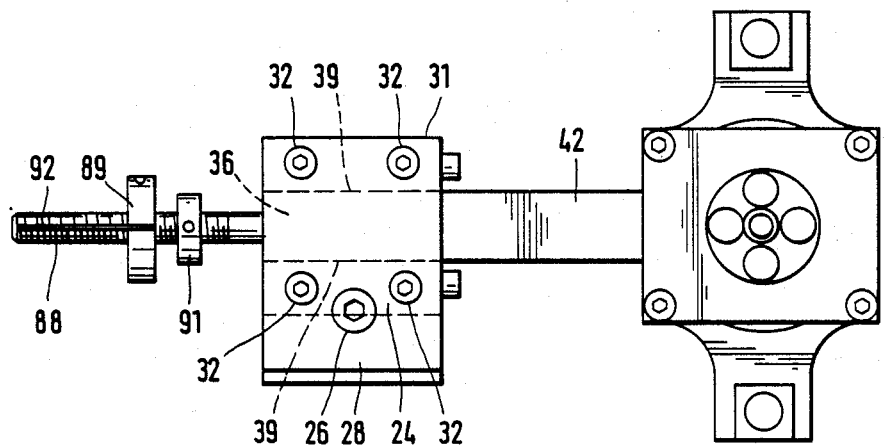
FIG. 2 is a view according to the arrow 2 in FIG. 1.
Figure 3:
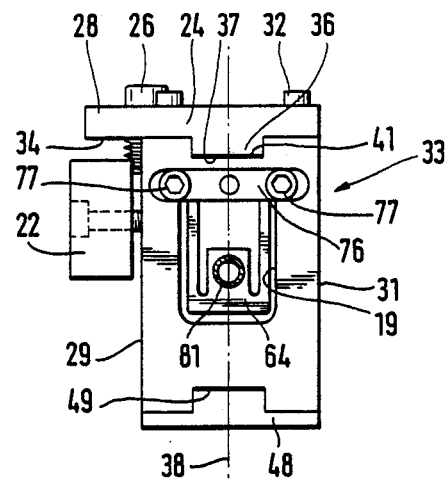
FIG. 3 is a section taken on the line 3,3 in FIG. 1.
Figure 4:
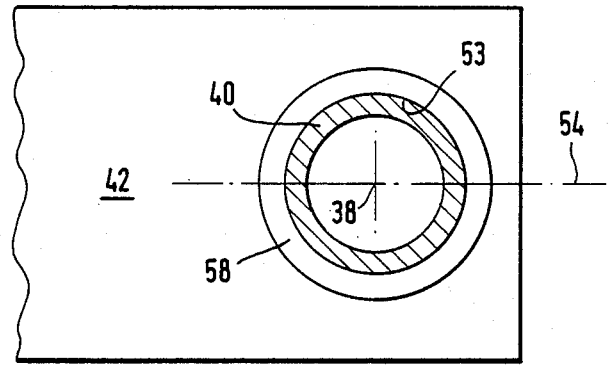
FIG. 4 is a section taken on the line 4,4 in FIG. 1.
Figure 9:
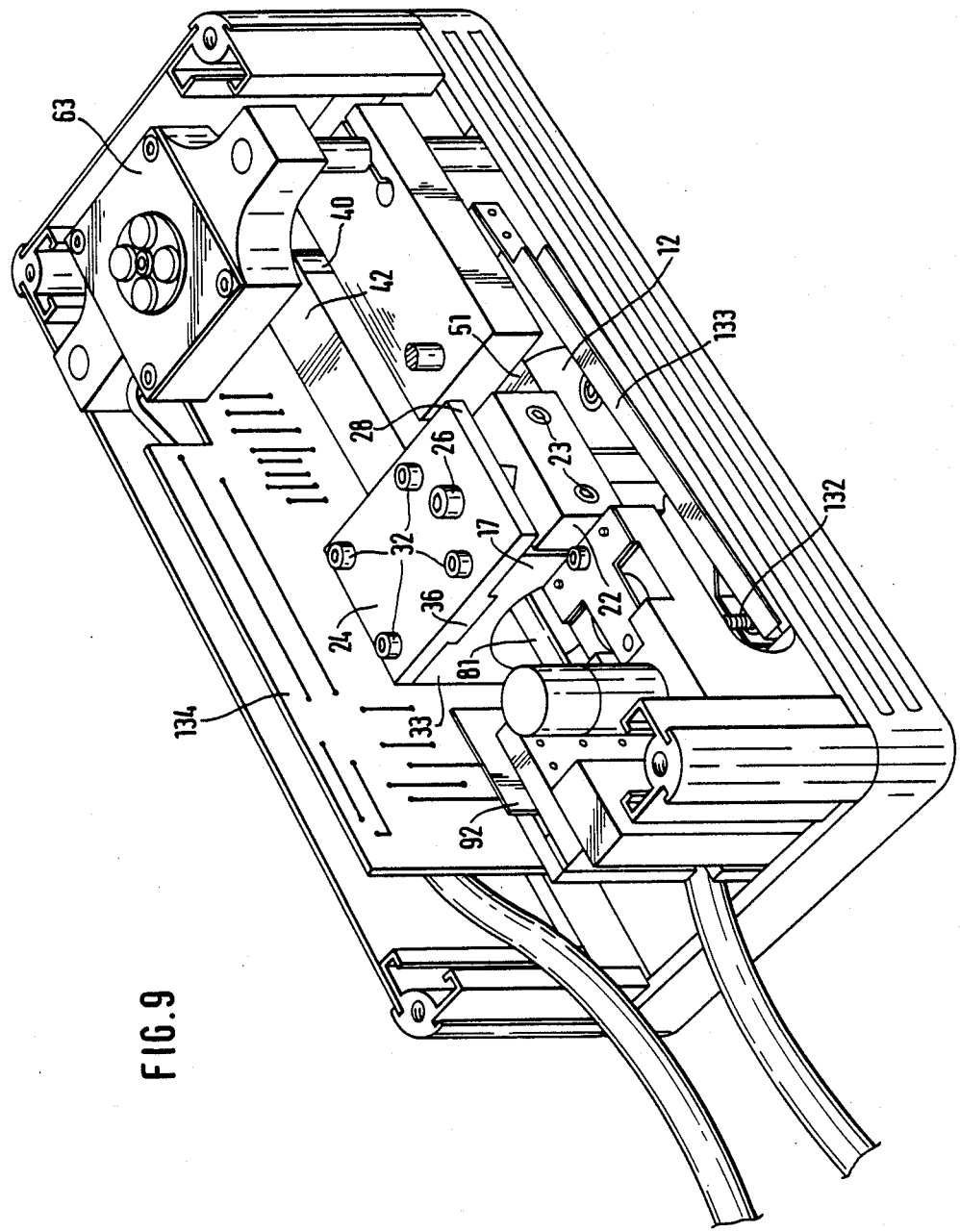
FIG. 9 is an overall perspective view of a hand-held nstrument, partly opened.

Screwed onto the bottom 11 of a hardness measuring instrument shown in FIG. 9 is a carrier plate 12 on which a stand 13 is fixed which has a quadratic cross-section and of which one edge 14 is facing forwardly in FIG. 1. Extending within it from an end face is a blind screwthreaded hole 16. Corresponding to the square cross-section of the stand 13, a triangularly prismatic guide 18 is incorporated into a metallic bearing block 17 from the latter's front face and intersects a longitudinal recess 19 (FIG. 3), which is why the lines of intersection 21 are shown in FIG. 1. A clamping block 22 is secured by screws 23 to what is in FIG. 1 the front face of the bearing block 17 and has a recess matching the guide 18 so that the square crosssection of the stand 13 can be accommodated and almost completely enclosed when the screws 23 are tightened, the stand 13 being clamped securely so that it is no longer displaceable in the direction of its height. The bearing block 17 comprises an upper clamping plate 24 in which there is a through bore aligned with the blind threaded hole 16. Traversing this through bore is the threaded shank of a screw 26 which is screwed into the blind hole 16. Between the under side of the clamping plate 24 and the upper end face of the stand 13 there is clamped a set of spring washers 27. As the screws 23 are slackened, the bearing block 17 moves down the stand 13 or upwards if the screw 26 is turned in the other direction. For the set of plate springs 27 and the screw 26, the clamping plate 24 has a projection 28 pointing to the left in FIG. 3 and which extends beyond the flat surface 29 shown on the left in FIG. 3. Close to the surface 29 and the flat surface 31 on the bearing block 27 which is parallel with it, the clamping plate 24 has four through bores to receive four screws 32 which are screwed into a member 33 which, as shown in FIG. 3, is shaped like a compressed H and which forms the core of the bearing block 17. Extending over its flat under side 34 and always at a rightangle to a geometrical longitudinal axis 38 of a small tube 40 which will be discussed later, the clamping plate 24 has a projection 36. The lateral flanks 39 of the projection 36 extend parallel with one another and vertically in the view shown in FIG. 3. According to FIG. 3, complementary to this configuration, the member 33 has a broad flat groove 41 disposed centrally and also perpendicular to the geometric longitudinal axis 38. Between the under side 37 and the bottom of the groove 41 is clamped the (according to FIG. 1) left-hand portion of a first leaf spring 42 which consists of beryllium/copper. The full scale drawing in FIG. 1 shows the front end 43 of the leaf spring 42. The rear end 44 is aligned with the back of the bearing block 17, producing a clamping area about 3 cm long which is very long in comparison with the overall length of the leaf spring 42 which is 88.5 mm. The emergence 46 of the leaf spring 42 from the bearing block 17 lies clearly in the flat side 47 which is on the right in FIG. 1 and which extends parallel with the geometric longitudinal axis 38. At the emergence 48 the projection 36 and the bottom of the groove 41 are sharply edged so that there is a clearly defined emergence 46, a clearly defined clamping effect and a clearly defined gap in respect of the geometric longitudinal axis 38. The leaf spring 42 is 0.1 mm thick, which is why it cannot be seen in the view in FIG. 3 which is likewise a full-scale drawing. It is 12 mm wide and the groove 41 is only a little wider so that it can accommodate the leaf spring 42 without any clamping. As FIG. 3 shows, the under side 37 and the bottom of the groove 41 are at right-angles to the geometric longitudinal axis 38.

Screwed to the under side of the body 33 is a clamping plate 48 which, except for the projection 28, is identical to but somewhat thinner than the clamping plate 24. By means of it and the groove 49 directed in opposition to the groove 41, an identical second leaf spring 51 is secured. Since the circumstances have been accurately described with reference to the leaf spring 42, they need not be repeated here. It should merely be pointed out that also this groove 49 must extend at right-angles to the geometrical longitudinal axis 38 and that the point of emergence 52 is at the same distance from the geometric longitudinal axis 38. Also the leaf spring 51 is of Cu Be 2 and is 0.1 mm thick. The other dimensions are also completely identical. The leaf springs 42, 51 are absolutely flat and have no inherent tension which might originate from unsuitable machining processes or from any bulges in them. The homogeneity of the properties is also assured in respect of forces of 0.1 to 0.01 milli-Newtons.

Figure 5:
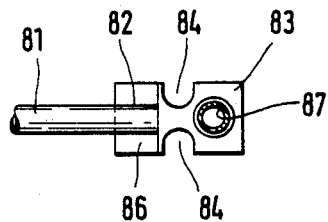
FIG. 5 is a section taken on the line 5,5 in FIG. 1.
Figure 6:
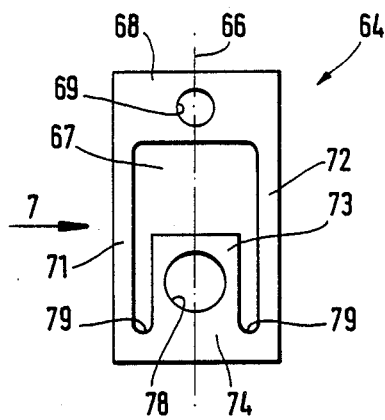
FIG. 6 is a view of a leaf spring which serves as a pivot joint.
Figure 7:
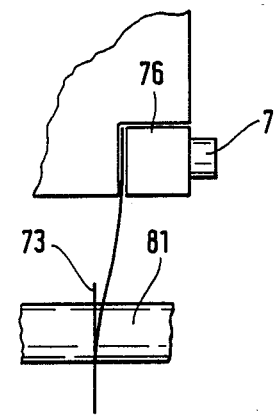
FIG. 7 is a view according to the arrow 7 in FIG. 6, partly broken away to illustrate the effect of the leaf pring according to FIG. 6.

In its free end zone, the leaf spring has a circular hole 53 6 mm in diameter. This, too, has been produced without stress at the edges, by etching. The hole 53 is both coaxial with the geometric longitudinal axis 38 and also exactly in the median line 54 of the leaf spring 42. By reason of this latter, there is no tendency to tilt. The leaf spring 51 comprises a hole 56 having exactly the same geometry. The small tube 40 consists of a titanium-/aluminium alloy so that it is both light and also rigid. It is produced by being cut from the solid. Its outside diameter corresponds to the diameter of the holes 53, 56. In the position of rest (neutral position), the small tube 40 is exactly coaxial with the geometric longitudinal axis 38. At the top, it has an external screwthread 57. The tube 40 is fitted into the hole 53 both by a small ring 58 being pushed on from above and also by a small ring 59 pushed on from the bottom. These separate rings are fastened to the tube 40 by a cold-setting glue. In the lower portion, at the height of the top of the leaf spring 51, the tube 40 has a circularly cylindrical shoulder 61, the under side of which is spaced apart from the right-hand end portion of the leaf spring 42 by exactly the same amount as the gap between the points of emergence 46 and 52. Under the shoulder 61, the tube 40 traverses the hole 56 and projects a little further downwards so that it fits into a coaxial sleeve 62. To the upper portion of this sleeve 62 and the shoulder 61, a little cold setting adhesive has been applied. "Cold" in this case naturally means a temperature which does not alter the structure of the leaf springs. Right at the bottom, the sleeve 62 grips a diamond 63 which constitutes the test body and screwed onto the external screwthread 57 is a coaxially arranged electric motor drive unit 63. This configuration would be adequate if one were sure that the geometric longitudinal axis 38 would always point to the centre of the earth during measurement. However, in order to be able to measure in any desired position, further measures are adopted: a leaf spring 64 is shown in FIG. 6 to a scale of 2:1. It is 14 mm wide, 25 mm high, is likewise made from Cu Be 2, is 0.1 mm thick and is given its shape by etching, without stress. It is completely flat when at rest. Its median plane 66 is also simultaneously in the geometric longitudinal axis 38 and the median line 54. It is symmetrical with the median plane 66. Its plane which is in the plane of the drawing in FIG. 6 is parallel with the geometric longitudinal axis 38. The (in plan view) rectangular leaf spring 64 has in it a centrally symmetrical cut-out 67 of an upside-down U-shape. Above this is a broad clamping zone 68 with a positioning hole 69 from which two narrow arms 71, 72 extend downwardly on either side. Separated from these by the longitudinal arms of the U is a central tongue 73 which merges at the bottom and via a cross web 74, into the arms 71, 72. Where the corners of the cut-out 67 may during operation be exposed to stress, a radius of 0.75 mm is provided. The leaf spring 64 is clamped in the longitudinal cut-out 19 by a clamping plate 76 in stress and curvature-free manner so that it hangs in a vertical direction, the clamping force being applied by two screws 77. The positioning hole 96 is traversed by a positioning stud which is rigidly connected to the member 33. As FIG. 6 shows, the boundary edges of the leaf spring 64—so far as they extend vertically—run parallel with the geometric longitudinal axis 38 or at right-angles to the latter if they extend horizontally. Etched centrally into the the central tongue 73 is a circular hole 78, the central axis of which intersects the geometric longitudinal axis 38. The radii 79 are substantially lower down than the bottom edge of the hole 78 and are at least 2 mm away from the bottom edge so that the middle tongue 73 can, according to FIG. 7, when standing approximately vertically, move leftwards when a force at the hole 78 exerts a force directed leftwardly in FIG. 7. The arms 71, 72 then extend in a slight S-shape. This force can be applied by a second tube 81 which passes through the hole 78 being fixed rigidly therein by the above-mentioned adhesion technique. For reasons of weight and rigidity, the tube is likewise made from an aluminium-titanium alloy and is thin-walled. Its outside diameter is 5 mm and it is about 11.5 cm long. Its end portion which is on the right in FIG. 1 has a short transverse slot 82 which lies exactly in the plane of the leaf springs 42, 51, which means at a right-angle to the geometric longitudinal axis 38. A leaf spring 83 which is short in comparison with the leaf springs 42, 51 but is just as wide and consists of the same materials, and which is stress free in the position of rest and which has been etched in its contours has, as shown in FIG. 5, two deep lateral depressions 84 between which remains roughly one-quarter of the width of the leaf spring. To the left of this there remains a fin 86 which is glued without stress into the slot 92. As FIG. 1 shows, the right-hand end of the tube 81 is at a slight distance of about 8 mm from the geometric longitudinal axis 38. The leaf spring 83 is exactly at right-angles to the geometric longitudinal axis 38 and has a hole 87 corresponding to and completely flush with the holes 53, 56. By means of the same technique of small rings or mating flange in one piece with the tube 40, adhesive fixing is carried out in the peripheral zone of the hole 87.

The tube 81 has on the left and external screwthread 88 onto which is screwed a counterweight 89 with a locking nut 91. Furthermore, there is on the external screwthread 88 a disc 92 for an electric damping device, the functioning of which is of no interest here. The counterweight 89 can be used to achieve such a fine equalization of weights that with the configuration shown in FIG. 1 there is no flexion of the leaf springs 42, 51, 83.

Figure 8:
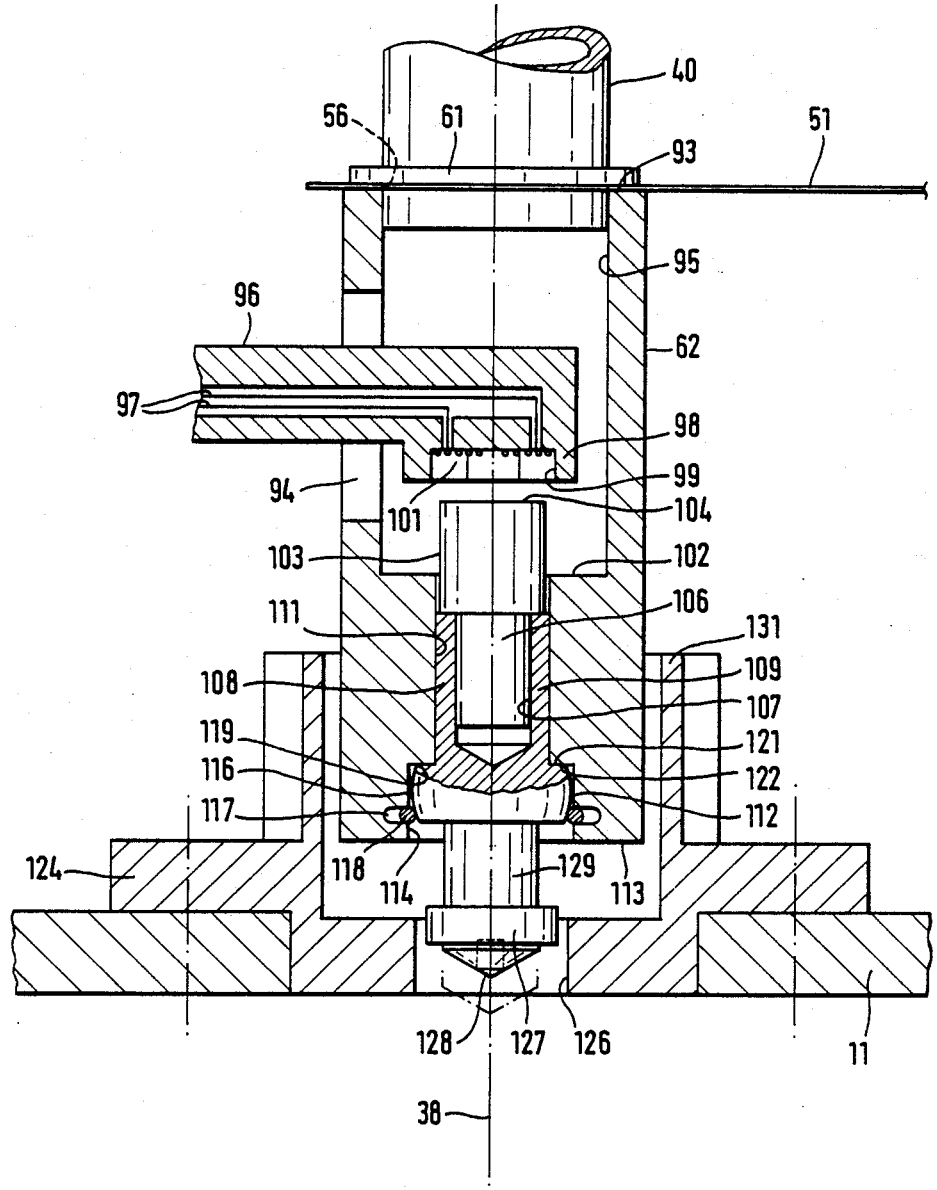
FIG. 8 is a section through the bottom right portion of the tube shown on the right in FIG. 1.

According to FIG. 8, which of course is shown to a scale of 10:1, we see at the top the tube 40 which is of 6 mm diameter. The sleeve 62 is secured by cold setting adhesive, in this sequence: collar 61 against the under side of which bears the leaf spring 51, the upper coaxial circularly cylindrical end face 93 of the aluminium sleeve 62 and the overlapping insertion of the very bottom portion of the tube 40 into an upper coaxial bore 93 of a farther downwardly extending stepped bore. According to FIG. 8, from the left, and according to FIG. 1, from the right, the sleeve 62 has in the remaining wall a large hole 94 into which projects an arm 96 rigid with the housing and in which there are electrical supply conductors 97 which lead to a probe head 98 which is comparable with the probe 77 in the Published Specification mentioned at the outset. In the coil space 99 coaxial with the geometric longitudinal axis 38 there is, as indicated, a coil 101. The bottom 102 of the bore 93 is considerably lower down than the bottom of the coil 101. Projecting upwardly from it is a measuring terminal 103 which consists of Al Cu Mg Pb F 38. Its end face 104 is finely finished and is at a right-angle to the geometric longitudinal axis 38. Its stud 106 fits securely in a bore 107 in a rotationally symmetrical diamond carrier 108. Its sleeve 109 fits in a coaxial continuation bore 111 which is not touched by the head of the measuring terminal 103. In the region below the end of the bore 107, the diamond carrier 108 has a convex bead 112 which projects outwardly. The bead 112 fits in a flat circularly cylindrical bore 114 which ends at the bottom end face 113 of the sleeve 62. The bore 114 has in its wall below the thickest point 116 of the bead 112 an inner peripheral groove 117 which extends at a right-angle to the geometric longitudinal axis axis 38 and in which there fits a snap ring 118 which in its position closer to the relaxed position projects at least partially into the bore 114 while in its completely relaxed position it does not project any farther therein than that corner 119 formed by the periphery of the bead 112 and circular shoulder 21 which is at right-angles to the geometric longitudinal axis 38 and which forms on the aside the transition with the peripheral surface of the sleeve 109. This shoulder 121 lies on the bottom 122 of the bore 114, in fact in clearly defined fashion, being also securely held in this position by the snap ring 118 which is subject to tension and which—since it is slipped over the thickest point 118—seeks to push the bead 112 upwardly and with it the entire diamond carrier 108.

Disposed in the housing bottom 11 and shown in FIG. 8 is the insert 124 which comprises a central bore 126 through which the mount 127 of a diamond 128 can pass. Via a cylinder 129, the mount 127 is in one piece with the bead 112. The insert 124 also has a pot-shaped part 131 which is open at the top, prevents movements in an undesired direction and so protects the bottom part of the sleeve 62 and the diamond carrier 108. This construction makes it possible to measure coaxially in the immediate vicinity of the diamond 128 and permits of a very simple but reproducible interchangeability of the diamond carrier 108. The end face 104 follows almost directly (for practical purposes absolutely directly) the movement of the diamond 128 and of its tip. The end face 104 corresponds to the downwardly facing surface of the part 74 mentioned in the German published specification already mentioned at the outset.

FIG. 9 shows the disposition of the device according to the invention. The spindle 132 and the leaf spring 133 correspond to the spindle 104 and the leaf spring 96 in the German published specification. Any necessary electronics are mounted on a circuit board 134.

If the measuring terminal 103 is of aluminium, then from the point of view of forces, there is no retroaction between it and the coil 101. However, if it is as preferred produced entirely or at least in its upper part from ferrite, then there is a substantially better sensitivity of the indication. No retroaction could be measured with ferrite, either.

The center of gravity of all masses acting on the tube 81, including its own mass, lies in the hole 78. The counterweight 89 is a circular metal disc and has an internal screwthread 136 which is screwed onto the external screwthread 88. In the plane of the drawing, a slot 137 is made exactly radially in the counterweight 89 from above, another slot 138 being made into it from below but which does not extend as far as the internal screwthread 136. Into each slot 137, 138 extends an internal screwthread 139, 141 into which a grub screw, not shown, is screwed. These maintain the disc 92 or the disc 142 rigid in its bottom right-hand or top right-hand corner as the case may be. Both disc 92, 142 are about 2.5 mm wide. The disc 142 is square and the disc 92 is 33 mm high. Both are 0.5 mm thick and very flat. They are of copper with a better than 95% copper content. If the small tube 40 with the test body 63 is moved up and down, then the discs 92, 142 move with their pivot point in the respective opposite direction about the middle tongue 73.

Figure 10:
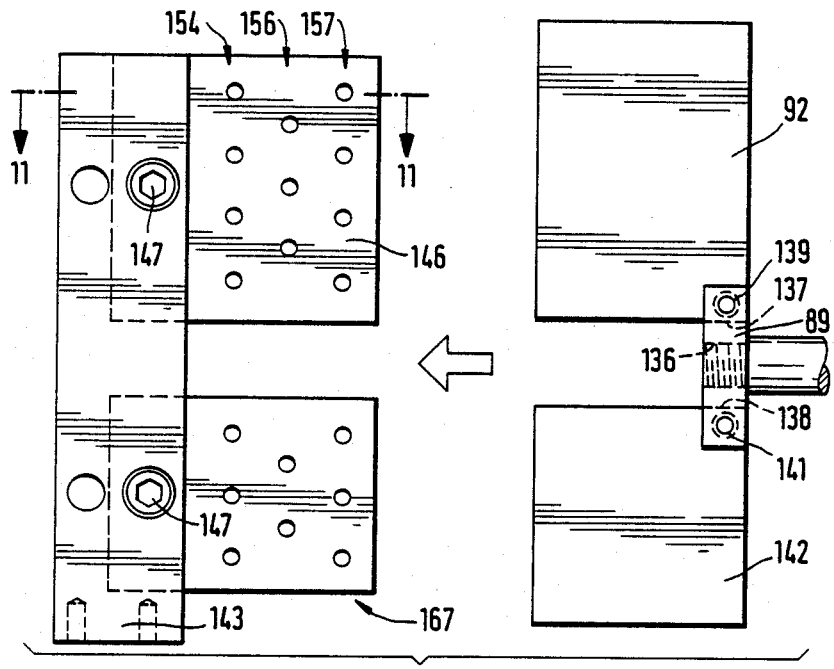
FIG. 10 shows an exploded side view of the damping device which is shown incompletely on the left in FIG. 1.
Figure 11:
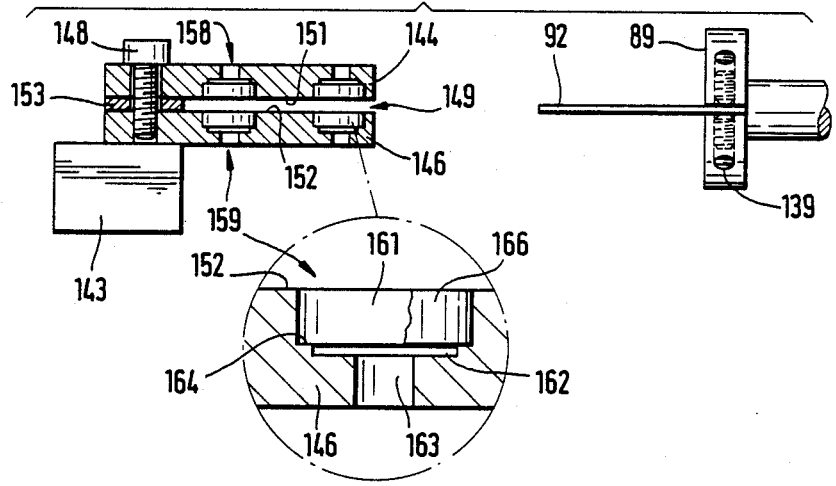
FIG. 11 is a section taken on the line 11, 11 in FIG. 10 together with the metal plate located in the slot.
Figure 12:
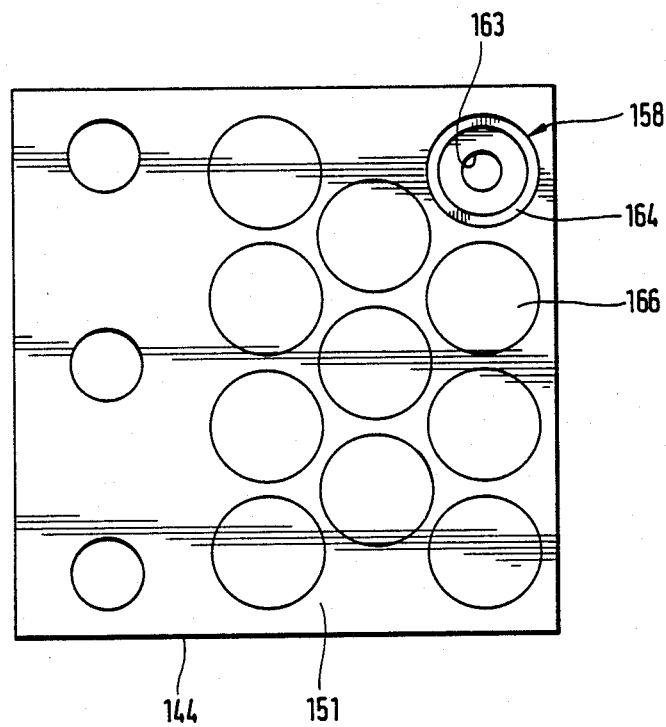
FIG. 12 is an interior view of a metal plate without magnets.

Screwed rigidly to the bottom 11 at the location shown in FIG. 9 is a solid rectangular metal profile 143. It is about 6.5 cm high and carries two upper plates 144, 146 which are of iron. They are each 4 mm thick and measure 3 cm square. Their marginal portion which is on the left in FIGS. 10 and 11 is screwed securely to the metal profile 143 from both sides by a screw 147 extending from the metal profile 143 and two screws 148 extending from the plate 144. The entire assembly therefore constitutes a very solid and above all rigid structure. To generate a slot 149 between the flat inner faces 151, 152, which are completely parallel with each other, a strip-like filler 153 is provided on the left-hand edge portion. This is likewise traversed by the screws 147, 148. The filler 153 is 1.3 mm thick so that when the plates 144, 146 are positioned exactly centrally in the slot 149, a gap of 0.4 mm remains on either side. The plates 144, 146 have in a vertical direction, in the area which is not covered by the metal profile 143 and immediately adjacent the filler 153, three vertically disposed rows of identical stepped bores 158, 159 which are exactly opposite one another. The row 154 and 157 has four bores and the row 156 has three bores, the rows being staggered in their disposition, in the manner shown in the drawing, in order to save space. By reason of this offset arrangement, the individual stepped bores can be positioned very close to one another. Each stepped bore 158, 159 is provided pairwise at the same height, one flush with another. The steps create a relatively large magnet space 161 and adjacent to this a space 162 of smaller diameter and, again adjacent to this, an exit bore 163. Between the magnet space 161 and the space 162, an annular shoulder 164 is created. The magnet space has a diameter of 6.1 mm and is 2.15 mm high. Seated in it is a circular permanent magnet 166 which is 2.15 mm high so that its upper face is exactly flush with the inner face 151, 152. It is glued into the magnet space 161, the annular shoulder 164 positioning it exactly and the space 162 and the exit bore 163 accommodate any excess adhesive. What is important is that all eleven permanent magnets 166 of one plate 144, 146 should have the same polarity.

For example, the inner surface 151 must be flush with the surface of the south pole and the same poles must also be located in the inner surface 152. No measurable difference was observed then if the like or opposite poles are opposite each other relative to the slot 149.

That which has been described here in detail for plates 144, 146, applies similarly to the two plate 176, of which only one can be seen in FIG. 10. The slot therein is aligned exactly with the slot 149 and the disc 142 is located entirely symmetrically in it. Complete symmetry means that no forces are generated which act on the tube 81 at right-angles to the plane of the drawing in FIG. 1.

The counterweight 89 combines the main mass. In addition, there is the smaller mass of the discs 92, 142. The total weight of all three components is around 15 g. The discs 92, 142 could also be produced from silver. However, it is questionable whether the approx. 10% greater electrical conductivity is worth the difference in price.

If the external screw thread 88 is allowed to end on the left of the counterweight 89, then the distance between the discs 92, 142 can be omitted and a single continuous disc provided which would then correspond to continuous plates 144, 146 having more permanent magnets 166.

The damping device described provides for aperiodic damping of even the current noise in the drive 63. From the point of view of magnitude, the device provides damping already at speeds of a few nanometers per tenth of a second.

The magnets used are products of Messrs. Krupp, where they are marketed under the trade mark Koermax.

I claim:

1. Device for a hardness measuring instrument, comprising
   a bar device having a pair of end portions and a middle portion,
   a test body supported on one end portion of said bar device,
   said middle portion being pivotable about a pivot center,
   a gently lowerable measuring device that works on the basis of probes for measuring the thickness of thin layers, and
   the improvement wherein:
   (a) a movable first part of an oscillation damping device is provided at one end portion of said bar device, and
   (b) said movable first part has a longitudinal extension aligned with the direction of movement of said test body.

2. Device according to claim 1, wherein with respect to said pivot center, the moment consisting of the weight of said first part of the damping device x a first length of said bar device as far as said pivot center is at least substantially equal to the weight acting at said end portion on said test body side x twice the length of said bar device as far as said pivot center.

3. Device according to claim 1, wherein said oscillation damping device is of a type unaffected by position.

4. Device according to claim 3, wherein said oscillation damping device is passive.

5. Device according to claim 4, wherein said oscillation damping device comprises permanent magnets.

6. Device according to claim 5, wherein said permanent magnets are glued in place by an adhesive material.

7. Device according to claim 5, wherein said permanent magnets are of the same type as the anisotropic permanent magnetic materials consisting of rare earth metal and cobalt.

8. Device according to claim 4, wherein said movable first part of said oscillation damping device is an electrically readily conductive metal plate.

9. Device according to claim 8, wherein said metal plate has an effective area that is very flat.

10. Device according to claim 8, wherein said metal plate is a copper plate.

11. Device according to claim 10, wherein said copper plate consists of high purity copper with a proportion of more than 95% copper.

12. Device according to claim 10, wherein said copper plate has a side with an area in the range from 5 to 30 sq.cm.

13. Device according to claim 12 wherein said area is between 10 and 20 sq. cm.

14. Device according to claim 1, comprising a housing and a second part of said oscillation damping device rigidly affixed thereto, said second part of said oscillation damping device comprising a rigid, solid carrier device for permanent magnets having outlet and inlet areas, said first part of said oscillation damping device comprising a metal plate having a face thereon, and said outlet and inlet areas of said second oscillation clamping device being spaced a small distance from and opposite said face of said metal plate.

15. Device according to claim 14, wherein said carrier device comprises at least one plate having a flat front face with depressions in which said permanent magnets are embedded.

16. Device according to claim 15, wherein said permanent magnets have outer faces aligned with said front face of said plate.

17. Device according to claim 15, wherein said carrier device comprises a second plate mutually parallel with said one plate, and said two mutually parallel plates consist of iron and are rigidly mounted a small distance from each other to form a narrow gap, and said metal plate is symmetrically disposed in said narrow gap.

18. Device according to claim 17, wherein said iron is soft iron.

* * * * *